United States Patent [19]

Pedersen

[11] 4,371,785
[45] Feb. 1, 1983

[54] METHOD AND APPARATUS FOR DETECTION AND ANALYSIS OF FLUIDS

[75] Inventor: Norman E. Pedersen, Wilmington, Mass.

[73] Assignee: Panametrics, Inc., Waltham, Mass.

[21] Appl. No.: 178,190

[22] Filed: Aug. 14, 1980

[51] Int. Cl.$^3$ .............................................. G01N 21/26
[52] U.S. Cl. .................................... 250/343; 250/345
[58] Field of Search ............... 250/343, 344, 345, 564, 250/565, 373; 356/436, 437, 438, 51

[56] References Cited

U.S. PATENT DOCUMENTS

| 3,887,473 | 6/1975 | Sternberg | 250/345 |
| 3,950,101 | 4/1976 | Dewey, Jr. | 250/345 X |
| 4,207,469 | 6/1980 | Hopkins et al. | 250/345 X |

*Primary Examiner*—Davis L. Willis
*Attorney, Agent, or Firm*—Lahive & Cockfield

[57] ABSTRACT

A photometric detection method and apparatus employ a variable beam modulation device, such as a planar rotating disk whose reflectance and transmittance with respect an incident beam of electromagnetic radiation vary with disk angular position, to form, from an incident beam of radiation, two amplitude modulated correlated component beams. Preferably the amplitudes of the component beams vary sinusoidally, 180° out of phase. In one embodiment, one of the component beams passes through a sample fluid, which absorbs a portion of the radiation at a wavelength characteristic of a selected component. The second component beam passes through a reference path and provides a reference relative to which changes in the sample fluid are measured. The component beams are combined and are directed onto a detector which produces an output proportional to the intensity of the combined beam. By properly selecting the parameters of the system, the AC component of the combined signal, if any, provides a measure of presence generally and if calibrated the relative density, of the selected sample fluid. In a second embodiment, a beam of polychromatic radiation passes through, and a portion thereof is absorbed by, the sample fluid before the beam impinges on a beam modulation device for forming the time-varying component beams. The thus formed component beams are filtered so that one component beam has energy substantially only at the sample fluid characteristic wavelength, and the other component beam has energy in energy bands which are unaffected by changes in the component of the sample fluid being measured. The component beams are combined and the AC component, if any, is detected and/or measured. In a third embodiment, a second movable element is supported in the path of the incident polychromatic radiation beam and serves as a variable, substantially monochromatic, filter for sequentially transmitting different energy bands to permit time sequential detection and/or analysis of a fluid medium at a plurality of wavelengths of interest.

26 Claims, 6 Drawing Figures

METHOD AND APPARATUS FOR DETECTION AND ANALYSIS OF FLUIDS

BACKGROUND OF THE INVENTION

The present invention pertains generally to the field of photometric detection and analysis, and more particularly to apparatus and methods for detecting and/or measuring the energy absorption by a fluid medium in a sample chamber.

In the qualitative and quantitative analysis of fluids, a well known analysis technique calls for a beam of electromagnetic radiation, such as visible light or infrared radiation, to be time-chopped (on-off modulated) to form a sample and a reference beam. The sample beam is directed through a sample of a fluid medium being examined; and selected components within the medium, if present, attentuate the energy of the incident beam at particular wavelengths characteristic of the selected fluid components. By measuring the amplitude of the sample beam, relative to the reference beam, after passing through the fluid at one or more wavelengths, it is possible to both detect and identify the selected fluid components and determine the density thereof.

Generally, however, these photometric detection and analysis measurement techniques attempt to measure small changes of signal which "ride" on a relatively large quiescent or base signal. Thus, changes of for example 0.1% or less in the overall signal are not unusual in order to accurately determine the quantity of selected fluids in the sample chamber. This happens because the amount of energy absorption at a wavelength of interest is relatively small compared to the magnitude of the incident and measured signals. Therefore, in order to make these measurements extremely precise, low noise, complex measurement techniques are generally employed.

As a result, at least one prior art system mechanically modulates, by successively blocking and unblocking, a reference and a sample beam respectively, for providing two correlated modulated waveform beams having a 180° out of phase AC component. These two beams, if not attenuated or if attenuated by the same amounts, can be combined to provide a single measurement signal having a constant amplitude. If however one of the beams is differentially attenuated, the combined measurement signal will have an AC component which can be measured and which is proportional to the difference in the amount of attenuation in the two amplitude modulated signals. This prior art apparatus improves the accuracy of the absorption measurement in a gas analysis system but suffers from the requirement of precision mechanical modulation of separate energy signals and the difficulties concommittant therewith.

In addition, prior art devices generally use a single interrogation wavelength during the course of an investigation. To make measurement determinations at a plurality of wavelengths, it is generally necessary to replace either the energy source or the monochromatic filter being used, and to recalibrate the system accordingly. This procedure can prove both time consuming and inefficient.

Objects of the present invention therefore are a fluid detection and/or analysis apparatus and method with improved precision, automatic operation, high efficiency, high reliable and relatively inexpensive manufacturing cost.

A further object of the present invention is a fluid detection and/or analysis apparatus and method having reduced complexity.

Yet a further object of the present invention is a fluid detection and/or analysis apparatus and method which automatically provide measurements at different wavelengths of interest.

SUMMARY OF THE INVENTION

The invention relates to a photometric detection apparatus for detecting in a fluid medium, at least one sample fluid component. The apparatus can be employed to simply detect the presence or absence of a sample component, or to provide an accurate measure of the density of the sample component. Associated with the sample component is a characteristic absorption wavelength of interest at which the component absorbs energy. The invention features a fluid sample chamber having an optical axis passing therethrough which is positioned in the path of a beam. The beam has components of energy at least at the characteristic wavelength and at a reference wavelength. The beam passes through the chamber along the optical path. A modulation element intercepts the beam exiting the sample chamber and divides the beam into at least first and second time-varying component beams. A first filter element is positioned in the path of the first component beam for passing substantially only radiation at the characteristic wavelength and a second filter element is positioned in the path of the second component beam for passing radiation at least at a reference wavelength but not including the radiation at the characteristic wavelength. The beams exiting the respective filters are combined and a detection device receives the combined beam and provides a measure of at least one selective characteristic thereof.

In a particular embodiment of the invention, the photometric detection apparatus modulation element has a rotatable planar element whose reflectance and transmittance properties vary with the angular position of the element about an element rotation axis. The modulation element also includes a member for rotating the element about the axis in the path of the beam exiting the sample chamber and thereby the incident radiation is divided into the first and second component beams. Preferably the rotatable planar element is rotated at a constant angular velocity.

The invention further features apparatus for detecting the combined signal and a synchronous detection and amplification element which is responsive to the angular position of the rotating element and to the output of the detector for synchronously measuring an AC component of the output signal from the detecter.

A second preferred embodiment of the invention relates to a photometric detection apparatus for detecting, in a fluid medium, at least one sample component of a sample fluid wherein the sample component has a characteristic absorption wavelength of interest. The apparatus features a beam modulation element in the path of a directed beam of electromagnetic radiation including radiation at at least the characteristic wavelength. The beam modulation element provides a reflected and a transmitted component beam whose intensities vary 180° out of phase with each other at the rate of repetitive movement of the beam modulation element. The beam modulation element has a planar member wherein the reflectance and transmittance with respect to the beam vary across its surface and a member for repetitively moving the planar member within the path of the beam. The apparatus further has a sample fluid holding chamber which has a first optical path passing therethrough, the chamber being positioned in the path of one of the reflected or transmitted component beams for passing that component beam through the sample chamber along the sample chamber optical path. A reference fluid holding chamber has a second optical path passing therethrough and the reference chamber is positioned in the path of the other of the reflected and transmitted components for passing that other component beam therethrough along the reference chamber optical path. The apparatus further features a member for combining the reflected and transmitted components after passage through the sample and reference chambers, and can have measurement elements for measuring or detecting the AC component, if any, of the combined beam.

The planar member is preferably a rotatable element which is positioned in the path of the beam from the radiation source and which has an incident planar surface whose reflectance and transmittance vary with the angular position of the element about an element rotation axis. Preferably the planar element is rotated at a constant rotational speed whereby the reflectance and the transmittance vary sinusoidally with the angular position. Thereby the reflected and transmitted component beams have respective intensities which vary sinusoidally, 180° out of phase.

In a third embodiment of the invention, the photometric detection apparatus is employed for detecting in a fluid medium at least one sample component of the fluid medium, the medium having a plurality of characteristic absorption wavelengths of interest. In this embodiment, the apparatus features a member for filtering the output of a beam source of electromagnetic radiation including radiation at at least two of said characteristic wavelengths to produce a time sequence of single component beams at successive ones of the plurality of characteristic wavelengths of interest. The filter has a planar element which has a plurality of narrow bandwidth filtering sections arranged in a predetermined manner and an element for selectively moving the planar element relative to the radiation beam to sequentially position each of the filtering sections in the path of the radiation beam. The filtering sections need not be discrete but may vary continuously. The radiation exiting the filter can be substantially bandwidth limited or, for example, monochromatic. The apparatus further features a beam modulation element in the path of the filtered beam for providing a reflected and a transmitted component whose intensities vary 180° out of phase at the rate of repetitive movement of the beam modulation element; and the beam modulation element further has a member whose reflectance and transmittance, with respect to the filtered beam, vary across its surface. A sample fluid holding chamber has a first optical path passing therethrough and a chamber is positioned in the path of one of the reflected and transmitted component beams from passing that one component beam through the sample chamber along the sample chamber optical axis. A reference fluid holding chamber has a second optical path passing therethrough and is positioned in the path of the other of the reflected and transmitted components for passing the other component beam therethrough along its optical path. A combining element combines the reflected and transmitted components after passage through the sample fluid and reference fluid holding chambers and a measuring or a detecting device is preferably provided for measuring or detecting respectively the AC component, if any, of the combined beam for each filter bandwidth of interest.

In another aspect, the invention features a method for detecting in a fluid medium, at least one sample component of the fluid, the sample component having at least one characteristic absorption wavelength of interest, having the steps of passing a polychromatic electromagnetic radiation beam through the fluid medium; modulating the radiation exiting the medium into two time varying components having a defined, interdependent, time-varying functional relationship; filtering a first of the two components to transmit substantially only the one characteristic wavelength of interest; filtering a second of the two components to transmit substantially only a wavelength band of the polychromatic radiation which is unaffected by changes in the sample component density; combining the two components with each other after the filtering steps; and measuring the AC components, if any, of the combined signal for detecting any absorption, and/or determining the amount of absorption, by the one sample component.

BRIEF DESCRIPTION OF THE DRAWINGS

Other objects, features, and advantages of the invention will appear from the following description of preferred embodiments of the invention and the drawings in which.

DESCRIPTION OF PREFERRED EMBODIMENTS

Figure 1:
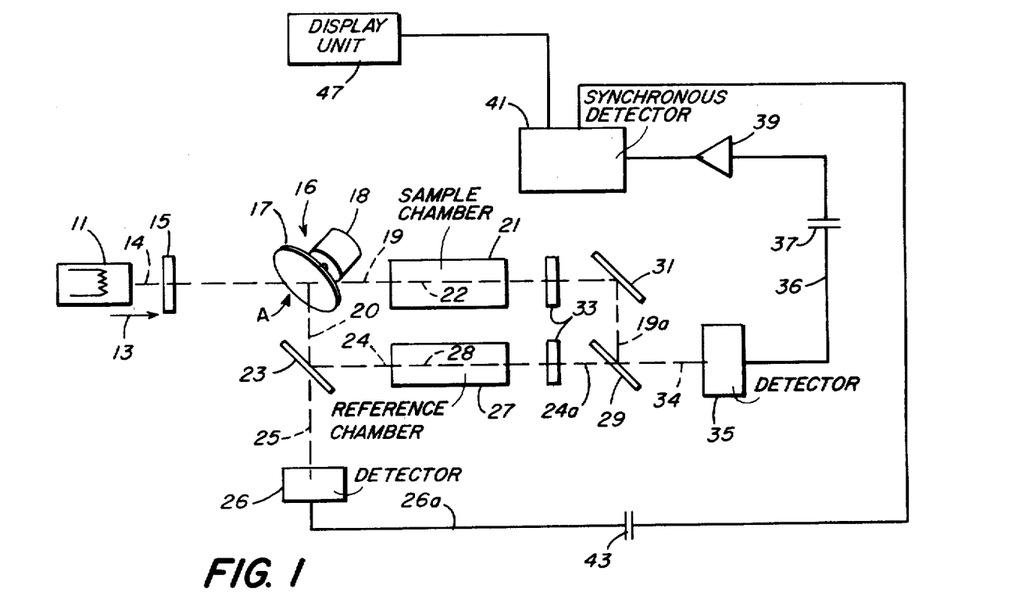
FIG. 1 is a schematic view of a gas detection and analysis apparatus in which the present invention is incorporated.

The photometric detection method and apparatus described herein can be advantageously employed in fluid detection systems, for example, a gas spectrometer or in liquid chromotography. Referring to FIG. 1, in a gas detection system, a source 11 of polychromatic infrared or other electromagnetic radiation directs a preferably collimated beam 14 outwardly in the direction of an arrow 13. The beam passes through a filter 15 which allows passage of only a narrow bandwidth of frequencies, including a wavelength for which a gas to be investigated has a characteristic absorption. The filtered beam is incident on a beam-modulation element 16. Illustrated element 16 has a planar disk-shaped member 17 which is rotated by a motor 18. Illustrated disk 17 rotates at a constant angular velocity although it will be clear to those practiced in the art that other speed relationships can be employed. Disk 17 is constructed so that its transmittance and reflectance, at wavelengths of interest, vary with the angular position of the disk. For example, the disk surface may include a metallic layer whose thickness, and accordingly its reflective properties, varies with angle. Preferably, however, the disk is dielectric coated to reduce energy losses.

The disk 17 divides the incident beam into a transmitted and a reflected beam, which follow paths 19 and 20 respectively. Since the reflectance (R) and transmittance (T) are related by the equation $R = 1 - T$ (assuming negligible absorption by the disk which is not a limitation of the apparatus), the variation in intensity of the reflected beam will be "oppositely directed" to that of the transmitted beam. Although the disk may be structured to produce any of a variety of mathematical relationships between the reflected and the transmitted beams, in this particular embodiment a sinusoidal relationship between the two is utilized. In other words, the amplitudes of the reflected and transmitted beams, when the disk is rotated at a constant angular velocity, vary sinusoidally, 180° out of phase with each other.

The transmitted, or sample, beam 19 is directed to and through a sample chamber 21 which encloses a sample of the gaseous medium being investigated. If one or more gases present in the sample chamber has an absorption characteristic at a particular wavelength of the incident radiation, the sample beam will be attenuated (a portion absorbed) during its passage through the sample chamber 21 along its optical path 22. The amount of attenuation will be proportional to the density of absorbing gas within the sample chamber and it is that attenuation which the apparatus is designed to accurately determine.

Meanwhile, the reflected beam 20 is directed onto a fixed beam splitter 23 which further divides the reflected beam into major and minor reference beams 24 and 25. The major reference beam 24 is reflected by the beam splitter 23, while the minor reference beam 25 is transmitted through the beam splitter and is incident upon a reference detector 26. The reference detector 26, a photodetector, produces, in response to minor reference beam 25, an AC signal over a line 26a of the same frequency as the modulation frequency of the sinusoidally varying, reflected beam 20. That AC signal will be used during synchronous detection as described in more detail below. The major reference beam 24 is directed to and through a second, or reference, chamber 27, along its optical path 28. Chamber 27 is preferably identical in structure to the sample chamber 21, and which contains a known reference gas which can include a known quantity of the gas to be investigated or detected.

At a beam combining element 29, which functions generally in the reverse manner of the beam splitter 23, an exiting reference beam 24a is combined with an exiting sample beam 19a, which in the illustrated embodiment has been reflected by a mirror 31 onto the beam combining element 29. When the beams 19a and 24a are combined, it is important that both beams have traversed substantially identical optical paths, to insure that the original 180° out of phase relationship has been maintained. Thus, when the attenuation in both optical paths is the same, which can under some circumstances be equated to the same quantity of sample gas in the sample and the reference chambers, the combined beam will, as described below according to the invention, have a constant intensity.

Figure 2:
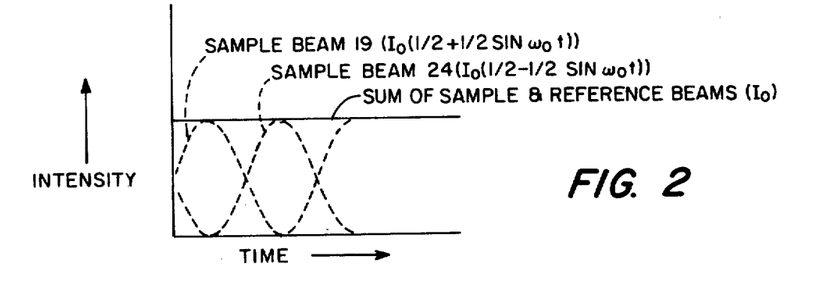
FIG. 2 is a graphical representation showing the respective amplitudes of the sample and reference beams and the resulting output of the detector in the absence of a sample gas differential absorption.

For example, assume that at point A the intensity of the original beam is $I_0$. The intensity of the transmitted portion (beam 19) (ignoring losses) will be $I_0(\frac{1}{2} + \frac{1}{2} \sin w_0 t)$, where $w_0$ is the angular speed of the rotating disk 17. The reflected portion (beam 20) will have an intensity $I_0(\frac{1}{2} - \frac{1}{2} \sin w_0 t)$. Upon emergence from their respective chambers (and ignoring the losses at beam splitter 23), the transmitted sample beam has an intensity $K_1 I_0 (\frac{1}{2} + \frac{1}{2} \sin w_0 t)$ and the reflected, reference beam has an intensity $K_2 I_0 (\frac{1}{2} - \frac{1}{2} \sin w_0 t)$ where $K_1$ and $K_2$ represent the attenuation of the respective beams in passing through the sample and reference chambers. If the attenuations are equal, or are somehow made equal ($K_1 = K_2 = K_0$), the combined beam will have an intensity equal to $K_0[I_0 (\frac{1}{2} + \frac{1}{2} \sin w_0 t) + I_0 (\frac{1}{2} - \frac{1}{2} \sin w_0 t)] = K_0 I_0$, where $K_0$ is a constant, time-independent value. Thus, $K_0$ represents the attenuation, if any, in the chambers 21 and 27, when, for example, the sample and reference chambers are identical in structure and contain equal amounts of identical gases. (See FIG. 2 for a graphic representation of these relationships.)

Referring to the illustrated embodiment of FIG. 1, variable neutral density filters 33 can be positioned in the paths of either or both of the exiting sample and the reference beams to balance their intensities during dynamic calibration of the apparatus, i.e., in a reference condition when both chambers 21, 27 contain selected amounts (which may be an empty condition) of the sample gas(es). That is, the intensity of one of the beams can be attenuated to compensate for transmission or absorption losses in the other beam, to insure that for the standard reference condition, a constant intensity is achieved upon combination to form beam 34. For example, the intensity of the exiting sample beam 19a can be attenuated to compensate for the slight loss in the reflected beam 20 at beam splitter 23.

Figure 3:
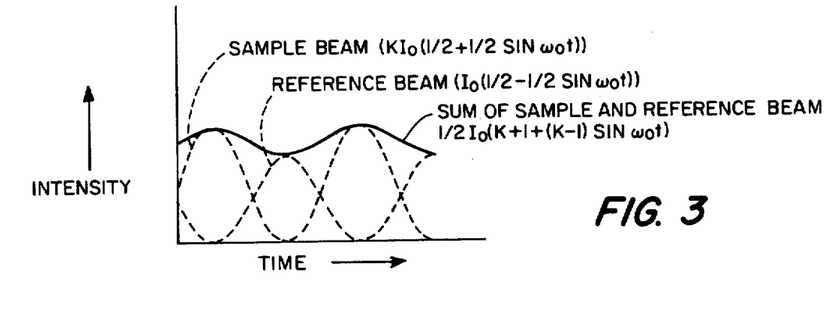
FIG. 3 is a figure similar to FIG. 2 showing the respective amplitudes of the sample and reference beams in the presence of sample gas differential absorption.

The combined beam 34 is directed onto a conventional detector 35, for example an infrared photodetector when infrared radiation is employed, which produces a voltage output over a line 36, proportional to the intensity of the radiation incident thereon. In the case of a constant intensity beam, the output of the detector will be a constant voltage. A different situation exists when there is a quantity of sample gas in the sample chamber 21 which effects a different absorption than the gas which was in sample chamber 21 during calibration of the system. Using the same assumptions as recited above regarding the intensity of the initial radiation, the intensity of the beam emerging from the sample chamber can be characterized as $K I_0 (\frac{1}{2} + \frac{1}{2} \sin w_0 t)$ where K is a positive factor less than unity different than $K_0$. Thus, the intensity of the recombined beam incident upon the detector will no longer be constant but will be represented by $[K I_0 (\frac{1}{2} + \frac{1}{2} \sin w_0 t) + I_0 K_0 (\frac{1}{2} - \frac{1}{2} \sin w_0 t)] = \frac{1}{2} I_0 [(K + K_0) + (K - K_0) \sin w_0 t]$ (see FIG. 3). This time varying amplitude has an AC component ($\frac{1}{2} I_0 [(K - K_0) \sin w_0 t]$) superimposed on the DC signal $\frac{1}{2}(K + K_0) I_0$. The AC component represents the difference between the gaseous medium being measured and the reference value employed during system calibration. It is therefore that AC value which carries the information of interest and the AC component output from the detector can be measured accurately using conventional amplification and synchronous detection techniques as follows.

Still referring to FIG. 1, a first coupling capacitor 37 couples the output of the detector 35 to an amplifier 39. The output of amplifier 39 is connected to a synchronous detector 41. The synchronous detector 41 also receives the AC component of the output signal from the reference detector 25 through a second coupling capacitor 43. The synchronous detector 41 thus synchronously detects the AC component of the signal from the detector 35 and produces an output proportional to the amplitude of the information AC signal from amplifier 39, to drive a display unit 47 such as, for example, an X-Y plotter, or a digital readout. The display unit thus indicates at least the amplitude of the AC component in the output of detector 35. Clearly in the case of a pure DC output from the detector 35, the first coupling capacitor 37 will block passage of the DC signal to the synchronous detector 41, resulting in a zero AC output therefrom.

With regard to the embodiment of FIG. 1, it should be noted that although the beam which was reflected by the disk was utilized as the reference beam and the beam transmitted through the disk was utilized as the sample beam, the reverse situation also would work equally well. Further, all optical surfaces in this illustrated embodiment, and in the embodiments illustrated in FIGS. 4 and 5, are preferably treated with an anti-reflection coating to avoid the generation of erroneous energy beams.

The preferred embodiments hereinbefore and hereinafter to be described enable the measurement and analysis of a gaseous medium by measuring the difference in attenuation between a reference signal and an unknown signal. The apparatus and method can also be employed simply to detect the presence of one or more specified gas components in the gaseous medium in which case the elements which measure the value of the difference would not be required and only the phase (or in some cases, the presence) of the AC component in the combined signal need be detected.

Figure 4:
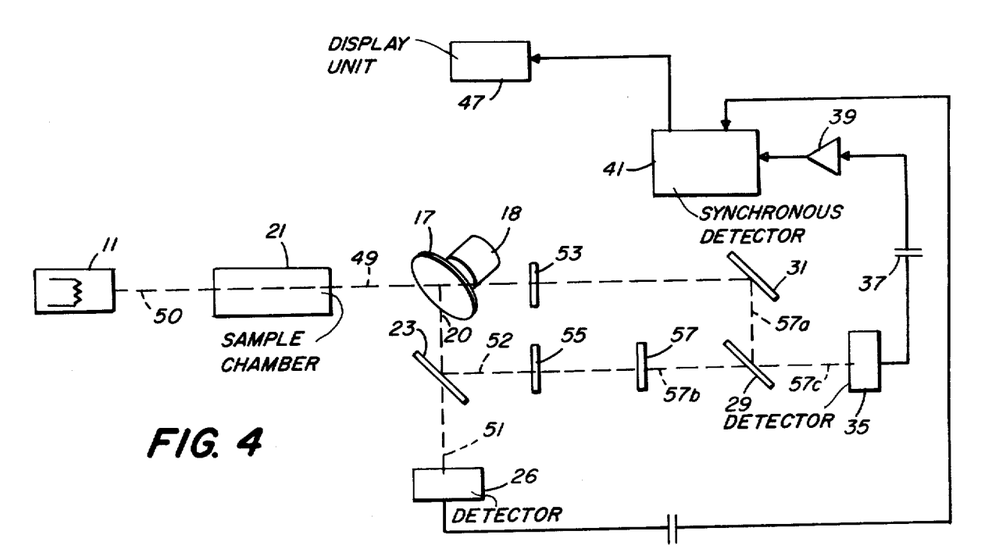
FIG. 4 is a schematic view of a second embodiment of a gas detection and analysis apparatus in which the present invention is incorporated.
Figure 5:
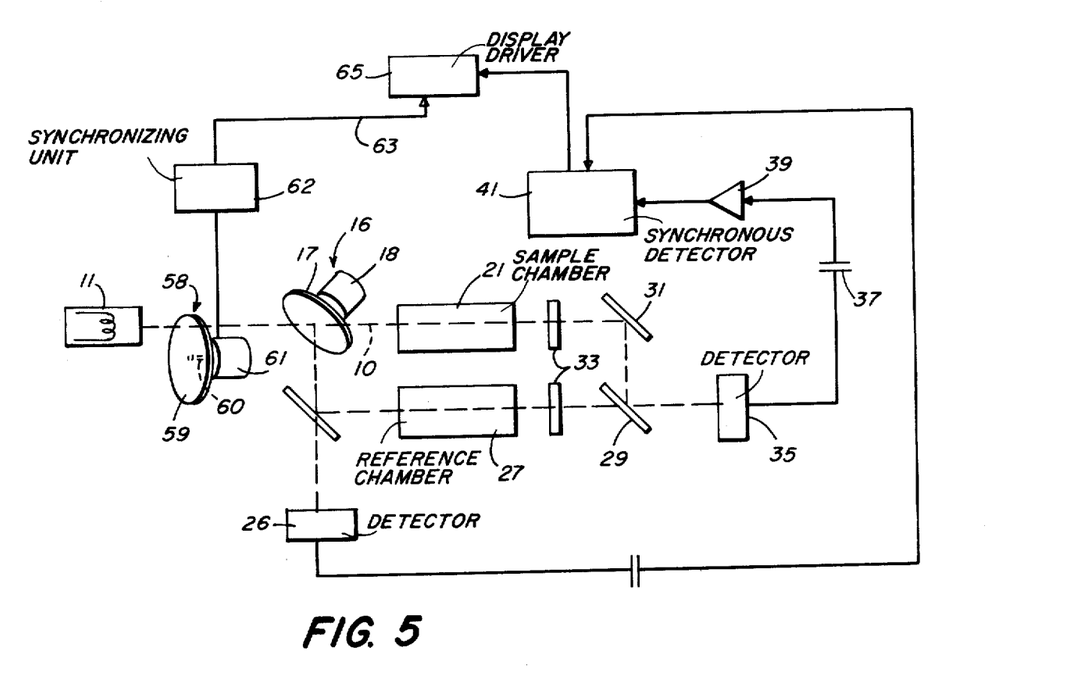
FIG. 5 is a schematic view of a third embodiment of the present invention.

Referring now to FIG. 4, in a second embodiment of the invention, the reference chamber 27 has been eliminated and the position of the sample chamber 21 has been moved to a location intermediate the source 11 and the beam modulating element, disk 17. A polychromatic energy beam 50 emanating from the infrared source passes through the sample chamber 21 and the exiting beam 49 is directed onto the rotating disk 17. In this manner, each of the wavelength components of beam 50 is subject to absorption by the gaseous medium within the chamber 21. At the rotating disk 17, the exit beam 49 is divided into the sample beam 19 (the transmitted component beam) and the reference beam 20 (the reflected component beam) in the same manner as described above with regard to FIG. 1. At the fixed beam splitter 23, the reference beam divides, as before, into two components, a major reference component 52 which is reflected, and a minor reference component 51 which is transmitted to the reference detector 26. Preferably, the intensities of the sample and reference beams vary sinusoidally, 180° out of phase. The sample beam 19 passes through a sample filter 53 which substantially blocks the passage of all wavelengths except for a narrow band of wavelengths of interest characteristic of the gase(es) of interest. At the same time, the major reference beam 52 passes through a reference filter 55 which substantially blocks the passage of all wavelengths except for a band of wavelengths at which the beam intensity is unaffected by, for example, density variations in the gas of interest being admitted to chamber 21.

To calibrate the apparatus of FIG. 4, a known amount of a reference gaseous medium, including the gas of interest is admitted to the sample chamber, and the sample and reference beams 57a and 57b respectively are then adjusted so that they will produce a constant amplitude combined beam 57c. A variable neutral density filter 57, positioned in FIG. 4 between the reference filter 55 and mirror 29 insures that the intensities of the radiation of the sample beam 57a and of the reference beam 57b combine to provide the constant amplitude output beam 57c. In other embodiments of the invention the filter 57 can be placed in the path of sample beam 57a. If the gas of interest is thereafter present in the sample chamber at a different density, the amount of absorption at the wavelength of interest changes, and the amplitude of the sample beam changes to a value different than that used to calibrate the apparatus reference signal. Then upon recombination, the resultant beam 57c will not be of constant amplitude but instead will have a sinusoidally varying component. The function of the detector 35, the synchronous detector 41, the reference detector 26, and the output device 47 are identical to the functions described with regard to FIG. 1.

Referring now to FIG. 5, a third embodiment of the present invention offers advantages in searching at multiple wavelengths of interest, for example for multiple gases within a given gaseous sample. A filtering element 58, a disk 59 coupled by a shaft 60 to a motor 61, is inserted between the source 11 and the beam-modulation element 16. The monochromatic filter 15 (FIG. 1) has been removed.

The disk 59 functions as a multiple passband filter in that the passband changes with the angular position of the disk. The band of wavelengths transmitted therethrough can be changed in either a continuous or a discrete mode (or even a combination thereof), and so long as a well-defined relationship exists between the band of wavelengths and, in the illustrated embodiment, the angular position of the disk 59, a precise relationship can be maintained corresponding to the wavelengths passed by the filter as a function of time. When the rate of rotation of the disk 59 is known as a function of time, the relationship becomes repetitive and periodic.

The remainder of the apparatus in this embodiment corresponds substantially to the embodiment of FIG. 1. The radiation transmitted through to the disk 17 is processed identically as in the case of the substantially monochromatic beam of FIG. 1. In effect, however, the apparatus of FIG. 5 will perform a sequence of identical measurements or detections, each at a different wavelength of interest. A synchronizing unit 62 responsive to filter element 58 provides an electrical reference signal over a line 63 to the electronic circuit 65 to correlate the information signal being provided by the synchronous detector 41 to the wavelength of radiation being passed by element 58. Synchronizing unit 62 thus indicates when the element 58 has made a transition from one wavelength of interest to another (in the discrete mode of operation), and unit 62 can be any of a variety of well known devices, such as, for example, a photosensor which senses markers appropriately positioned on the surface of the disk element 58 and produces distinctive outputs in response thereto. Alternatively the synchronizing unit can employ a shaft position encoder coupled to the shaft 60. The output of the encoder identifies the angular position of the shaft, and therefore the wavelength that is passed at that position.

If the reference gas has different absorption characteristics at the different wavelengths of interest, these differences must be measured, and thereafter taken into account during calibration of the apparatus. In particular, then, circuit 65, in response to the detected differential between the sample and reflected beams, will produce an output which accurately represents the amount of relative attenuation by the sample gas at each wavelength. For example the circuit 65 may employ several subcircuits, each corresponding to a different wavelength of interest, which are sequentially addressed or selected by the synchronizing unit 62 reference signals over line 63. Each subcircuit, in its turn, generates an output for the display appropriate for the detected signal at that wavelength.

The embodiments described thus far have all related to fluid photometric detection apparatus employing gases as the unknown or sample fluid. As noted above, the photometric detection systems with which the invention can be advantageously employed, are not limited to gas systems but also include liquid systems, for example ultraviolet absorption detectors for use in high speed liquid chromatography. The invention can be advantageously employed in these other fluid detection systems for providing superior detection and analysis capability.

Figure 6:
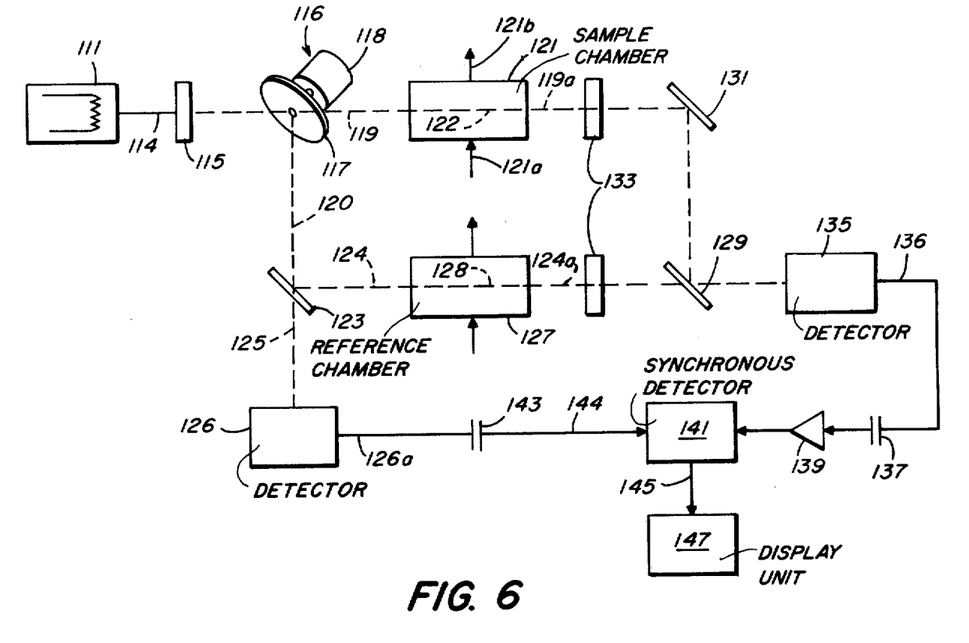
FIG. 6 is a schematic view of an ultraviolet detector according to the invention for use in liquid chromatography.

Referring to FIG. 6, an ultraviolet absorption detector for use in liquid chromatography resembles substantially identically the gas detection apparatus of FIG. 1. The illustrated liquid chromatography system has a source 111 of polychromatic energy including energy at least in the ultraviolet range. The source directs its radiation, preferably in a collimated beam 114, toward a filter 115 which allows passage of only a narrow bandwidth of frequencies. Included within that bandwidth is a wavelength to which the liquid being examined has a characteristic absorption. The filtered beam is incident on a beam modulation element 116. As in earlier embodiments, the illustrated element 116 has a planar disk shaped member 117 which is rotated by a motor 118. The illustrated disk 117 rotates at a constant angular velocity in this embodiment and is constructed so that its transmittance and reflectance, at wavelengths of interest, vary sinusoidally with the angular position of the disk. Preferably the disk has a metallic layer whose thickness, and accordingly its reflective properties, varies with angle. The disk is coated with a dielectric composition to reduce energy losses.

The disk 117 divides the incident beam into a transmitted and a reflected beam which follow paths 119 and 120 respectively. Thus, beams 119 and 120, as described in connection with the embodiment of FIG. 1, vary in intensity so that the reflected beam will be "oppositely directed" to the intensity of the transmitted beam. The transmitted, or sample beam 119 is directed to and through a sample chamber 121 which houses the liquid medium being investigated. Typically, chamber 121 has an inlet port 121a and an outlet port 121b into which and out of which, respectively, the liquid being examined flows.

In a typical system, as is well know in the art, a Z configuration sample chamber can be used. This is a classical type of chamber in which the mobile phase comes in one end of the chamber, sweeps the window, and goes down the cell cavity and out the other end. To minimize noise and drift due to flow variations, however, an H cell configuration can also be used. If one or more of the fluid components present in the sample chamber has an absorption characteristic at a particular wavelength of the incident radiation, the sample beam will be attenuated (corresponding to a portion of it being absorbed) during its passage through the sample chamber 121 along an optical path 122. The amount of attenuation in the liquid system, as in the gaseous system, will be proportional to the density of the absorbing fluid components within the sample chamber, and it is that attenuation which the apparatus is designed to accurately detect.

At the same time, the reflected beam 120 is being directed onto a fixed beam splitter 123 which further divides that beam into major and minor reference beams 124 and 125 respectively. The major reference beam 124, the reflected beam, is directed toward a reference chamber 127. The minor reference beam 125 is directed to a reference detector 126. The reference detector 126, typically a photodetector (sensitive to ultraviolet in this embodiment), produces in response to the minor reference beam 125 an AC signal over a line 126a of the same frequency as the modulating frequency of the sinusoidally varying reflected beam 120. That AC signal, as described above, is used for synchronously detecting the AC component of what will become the combined output of the system.

As noted above, the major reference beam is directed toward the reference chamber 127 and in particular an optical path 128 through the reference chamber. Reference chamber 127 is preferably identical in structure to the sample chamber 121 and contains a known reference fluid which can include a a known quantity of the fluid component(s) to be investigated or detected.

An exiting reference beam 124a is combined with an exiting sample beam 119a which, in the illustrated embodiment, has been reflected by a mirror 131 onto the beam combining element 129. When beams 119a and 124a are combined, both beams will have traveled substantially the same length paths and hence will have suffered substantially the same attenuation due to the naturally occurring attenuating factors in the field through which the beams pass. The beams are directed onto a photodetecting element 135 which is, in the illustrated embodiment, an ultraviolet sensitive photodetector and which produces a voltage output over a line 136 which is proportional to the intensity of the radiation incident thereon. As in the embodiment of FIG. 1, it may be desirable to provide additional filtering such as neutral density filters 33 to equalize the time varying components of the system so that the output of the detector 135 has no AC component when the densities of the sample liquids being examined in the reference and sample chambers 127 and 121 respectively are equal.

The output of detector 135 over line 136 is coupled through a capacitor 137 to an amplifier 139. The output of amplifier 139 is applied to a synchronous detector 141 which also receives the AC component over the output signal from reference beam 125 through a second coupling capacitor 143 over a line 144. The synchronous detector 141 thereby, as described in connection with FIG. 1 synchronously detects the AC component of the signal from the detector 135 and produces an output over a line 145 proportional to the amplitude of the information AC signal component from amplifier 139. That output drives a display unit 147. The display unit thus indicates at least the amplitude of the AC component and the output of detector 135. It is this AC component which provides a measure of the sample liquid component being examined (or samples being examined) in the sample chamber 121.

It should be evident that this embodiment is substantially identical to the embodiment of FIG. 1. In a similar manner, the several embodiments described in connection with FIGS. 4 and 5 can also be adapted to a liquid detection system for use in high speed liquid chromotography. Thus, in the embodiment of FIG. 4, sample chamber 21 can be replaced by a Z type or H type configuration liquid chamber and in the embodiment of FIG. 5 the sample and reference chambers 21 and 27 can be made to correspond to the chambers 121 and 127 of FIG. 6.

The illustrative embodiments of the figures each describe a complete detection and analysis apparatus and method. However, subassemblies of the illustrated detection and analysis apparatus and method can be used in existing analysis and/or detection apparatus as described herein to upgrade an existing apparatus. Thus, as various changes can be made in the embodiments set forth above without departing from the scope of the invention, it should be understood that the above description, including the accompanying drawings, shall be interpreted as illustrative and not in a limiting sense. Additions, subtractions, deletions and other modifications of the illustrated embodiments would be obvious to one practiced in the art and are within the scope of the following claims.

What is claimed is:

1. A photometric analysis apparatus for analyzing a fluid medium having at least one sample component having a characteristic absorption wavelength of interest, comprising:

a beam source of electromagnetic radiation including radiation at least at said one characteristic wavelength and at a reference wavelength, a fluid sample chamber having an optical path passing therethrough, means for positioning said chamber in the path of said beam for passing said beam through said chamber along said optical path, means for modulating said beam exiting said chamber for forming at least first and second time-varying component beams, first filter means in the path of the first component beam for passing substantially only radiation of said characteristic wavelength, second filter means in the path of the second component beam for passing radiation at at least said reference wavelength and not including said characteristic wavelength, means for combining said first and second wavelength component beams exiting said respective filter means, and means for measuring selected characteristics of said combined beam.

2. The photometric analysis apparatus as set forth in claim 1 wherein said electromagnetic radiation is within the infrared spectrum.

3. The photometric analysis apparatus as set forth in claim 2 wherein said dividing means comprises a rotatable planar element having reflectance and transmittance properties which vary with the angular position of said element about an element rotation axis; and means for rotating said element about said axis in the path of said chamber exit beam;

whereby the incident radiation beam is divided into said first and second component beams.

4. The photometric analysis apparatus as set forth in claim 3 wherein said rotating means rotates said element at a constant rate.

5. The photometric analysis apparatus as set forth in claim 4 wherein said reflectance and transmittance properties vary such that said first and second components have intensities which vary sinusoidally, 180° out of phase with each other.

6. The photometric analysis apparatus as set forth in claim 5 wherein said combining means comprises:

a radiation detector, means for directing said exiting first and second components from said filter means onto said detector, said detector providing an electrical signal output proportional to the sum of the intensities of said exiting components; and synchronous detection and amplification means responsive to said rotation means and to the output of said detector for measuring an AC component of the output signal.

7. A photometric analysis apparatus for analyzing a fluid medium having at least one sample component having a characteristic absorption wavelength of interest, comprising:

a beam source of electromagnetic radiation including radiation at at least said one characteristic wavelength for providing a directed beam containing said characteristic wavelength;

beam modulation means in the path of said beam for providing a reflected and a transmitted component beam whose intensities vary 180° out of phase at the rate of repetitive movement of said beam modulation means, said means comprising a planar member having a reflectance and a transmittance with respect to said beam which vary across its surface, and means for repetitively moving said member within said path, a sample fluid holding chamber having a first optical path passing therethrough, means for positioning said sample chamber in the path of one of said reflected and transmitted component beams for passing said one component through said sample chamber along the sample chamber optical path passing therethrough, a reference fluid holding chamber having a second optical path passing therethrough, means for positioning said reference fluid chamber in the path of the other of said reflected and transmitted components for passing said other component beam through said reference chamber along the reference chamber optical path passing therethrough, means for combining said reflected and transmitted components after passage through said sample fluid holding chamber and said reference fluid holding chamber; and means for measuring the AC component of said combined beam.

8. The photometric analysis apparatus as set forth in claim 7 wherein said member comprises a rotatable planar element supported in the path of said beam and having an incident planar surface whose reflectance and transmittance vary with the angular position of said element about an element rotation axis; and said moving means is a motor operatively connected to rotate said planar element about said rotation axis.

9. The photometric analysis apparatus as set forth in claim 8 wherein said reflectance and transmittance vary sinusoidally with angular position whereby said reflected and transmitted components have respective intensities which vary sinusoidally, 180° out of phase.

10. The photometric analysis apparatus as set forth in claim 9 wherein said motor rotates said element at a constant angular velocity.

11. A photometric analysis apparatus for analyzing a fluid medium having at least one sample component, said medium having a plurality of characteristic absorption wavelengths of interest, comprising:
 a beam source of electromagnetic radiation including radiation at at least two said characteristic wavelengths;
 means for filtering said beam to produce a sequence of single component beams at successive ones of said plurality of characteristic wavelengths, said filtering means having
  a planar element having a plurality of narrow bandwidth filtering sections arranged in a predetermined manner, and
  means for selectively moving said element relative to said radiation beam to sequentially position each respective filtering section in the path of said radiation beam;
 beam modulation means in the path of said filtered beam for providing a reflected and a transmitted component beam whose intensities vary 180° out of phase, at the rate of repetitive movement of said beam modulation means, said modulation means comprising
  a member having a reflectance and a transmittance with respect to said filtered beam which vary across its surface, and
  means for repetitively moving said member within said path,
 a sample fluid holding chamber having a first optical path passing therethrough,
 means for positioning said sample chamber in the path of one of said reflected and transmitted component beams for passing said one component through said sample chamber along the sample chamber optical path passing therethrough,
 a reference fluid holding chamber having a second optical path passing therethrough,
 means for positioning said reference fluid chamber in the path of the other of said reflected and transmitted components for passing said other component through said reference chamber along the reference chamber optical path passing therethrough,
 means for combining said reflected and transmitted components after passage through said sample fluid holding chamber and said reference fluid holding chamber; and
 means for measuring the AC components of said combined beam for each filtering section.

12. The photometric analysis apparatus as set forth in claim 11 wherein said filter sections are arranged in a circumferential direction circularly around the center of a disk element and said element moving means comprises a motor for rotating said disk in a predetermined sequence about a central rotation axis.

13. A photometric analysis apparatus for analyzing a fluid medium having at least one sample fluid component, said medium having a plurality of characteristic absorption wavelengths of interest, comprising:
 a beam source of electromagnetic radiation including radiation at at least two said characteristic wavelengths;
 means for filtering said beam to produce a sequence of single component beams at successive ones of said plurality of characteristic wavelengths, said filtering means having
  a rotatable planar element having a varying narrow bandwidth filtering characteristic arranged in a predetermined manner; and
  means for selectively moving said element relative to said radiation beam to position said respective filtering characteristics in the path of said radiation beam;
 beam-forming means supported in the path of said filtered beam for providing a first and a second component beam whose intensities vary 180° out of phase with each other,
 a sample fluid holding chamber having a first optical path passing therethrough positioned in the path of one of said first and second components for passing one said component through said sample chamber along the sample chamber optical path passing therethrough,
 a reference fluid holding chamber having a second optical path passing therethrough positioned in the path of the other of said first and second components for passing said other component through said reference chamber along the reference chamber optical path passing therethrough,
 means for combining said first and second components after passage through said sample fluid holding chamber and said reference fluid holding chamber; and
 means for measuring the AC components of said combined beam for selected filter bandpass characteristics.

14. A photometric detection apparatus for detecting, in a fluid medium, at least one sample fluid component having a characteristic absorption wavelength of interest, comprising:
 a fluid sample chamber having an optical path passing therethrough,
 means for positioning said chamber in the path of a beam of electromagnetic radiation, including radiation at least at said one characteristic wavelength and at a reference wavelength, for passing said beam through said chamber along said optical path,
 means for modulating said beam exiting said chamber for forming at least first and second time-varying component beams,
 first filter means in the path of the first component beam for passing substantially only radiation of said characteristic wavelength,
 second filter means in the path of the second component beam for passing radiaton at at least said reference wavelength and not including said characteristic wavelength, and
 means for combining said first and second wavelength component beams exiting said respective filter means for providing a detection signal characteristic of the quantity of said at least one sample fluid component.

15. The photometric detection apparatus as set forth in claim 14 wherein said dividing means comprises a rotatable planar element having reflectance and transmittance properties which vary with the angular position of said element about an element rotation axis; and means for rotating said element about said axis in the path of said chamber exit beam;

whereby the incident radiation beam is divided into said first and second component beams.

16. The photometric detection apparatus as set forth in claim 15 wherein said reflectance and transmittance properties vary such that said first and second components have intensities which vary sinusoidally, 180° out of phase with each other.

17. A photometric detection apparatus for detecting, in a fluid medium, at least one sample fluid component having a characteristic absorption wavelength of interest, comprising:

beam modulation means in the path of a directed beam of electromagnetic radiation including radiation at at least said one characteristic wavelength, for providing a reflected and a transmitted component beam whose intensities vary 180° out of phase at the rate of repetitive movement of said beam modulation means, said means comprising a planar member having a reflectance and a transmittance with respect to said beam which vary across its surface, and means for repetitively moving said member within said path, a sample fluid holding chamber having a first optical path passing therethrough, means for positioning said sample chamber in the path of one of said reflected and transmitted component beams for passing said one component through said sample chamber along the sample chamber optical path passing therethrough, a reference fluid holding chamber having a second optical path passing therethrough, means for positioning said reference fluid chamber in the path of the other of said reflected and transmitted components for passing said other component beam through said reference chamber along the reference chamber optical path passing therethrough, and means for combining said reflected and transmitted components after passage through said sample fluid holding chamber and said reference fluid holding chamber for providing a detection signal characteristic of the quantity of said at least one sample fluid component.

18. The photometric detection apparatus as set forth in claim 17 wherein said member comprises a rotatable planar element supported in the path of said beam and having an incident planar surface whose reflectance and transmittance vary with the angular position of said element about an element rotation axis; and said moving means is a motor operatively connected to rotate said planar element about said rotation axis.

19. A photometric detection apparatus for detecting, in a fluid medium, at least one sample fluid component, said medium having a plurality of characteristic absorption wavelengths of interest, comprising:

means for filtering an incident beam of electromagnetic radiation including radiation at at least two of said characteristic wavelengths to produce a sequence of single component beams at successive ones of said plurality of characteristic wavelengths, said filtering means having a planar element having a plurality of narrow bandwidth filtering sections arranged in a predetermined manner, and means for selectively moving said element relative to said radiation beam to sequentially position each respective filtering section in the path of said radiation beam;

beam modulation means in the path of said filtered beam for providing a reflected and a transmitted component beam whose intensities vary 180° out of phase, at the rate of repetitive movement of said beam modulation means, said modulation means comprising a member having a reflectance and a transmittance with respect to said filtered beam which vary across its surface, and means for repetitively moving said member within said path, a sample fluid holding chamber having a first optical path passing therethrough, means for positioning said sample chamber in the path of one of said reflected and transmitted component beams for passing said one component through said sample chamber along the sample chamber optical path passing therethrough, a reference fluid holding chamber having a second optical path passing therethrough, and means for positioning said reference fluid chamber in the path of the other of said reflected and transmitted components for passing said other component through said reference chamber along the reference chamber optical path passing therethrough, means for combining said reflected and transmitted components after passage through said sample fluid holding chamber and said reference fluid holding chamber for providing a detection signal, time sequentially characteristic of the fluid medium absorption for each filtering section.

20. A photometric detection apparatus for detecting, in a fluid medium, at least one sample fluid component, said medium having a plurality of characteristic absorption wavelengths of interest, comprising:

means for filtering a beam of electromagnetic radiation including radiation at at least two said characteristic wavelengths to produce a sequence of single component beams at successive ones of said plurality of characteristic wavelengths, said filtering means having a rotatable planar element having a varying narrow bandwidth filtering characteristic arranged in a predetermined manner; and means for selectively moving said element relative to said radiation beam to position said respective filtering characteristics in the path of said radiation beam;

beam-forming means supported in the path of said filtered beam for providing a first and a second component beam whose intensities vary 180° out of phase with each other, a sample fluid holding chamber having a first optical path passing therethrough positioned in the path of one of said first and second components for passing one said component through said sample chamber along the sample chamber optical path passing therethrough, a reference fluid holding chamber having a second optical path passing therethrough positioned in the path of the other of said first and second components for passing said other component through said reference chamber along the reference chamber optical path passing therethrough, means for combining said first and second components after passage through said sample fluid holding chamber and said reference fluid holding chamber for providing a time sequential detection signal characteristic of said fluid medium at said successive filter frequencies.

21. A method for detecting in a fluid medium, at least one sample component of said fluid, said one sample component having at least one characteristic absorption wavelength of interest, comprising the steps of:
A. passing a polychromatic electromagnetic radiation beam through said fluid medium;
B. dividing radiation exiting said medium into two time-varying components having a defined interdependent time-varying functional relationship;
C. filtering a first of said two components to transmit substantially only the one characteristic wavelength;
D. filtering a second of said two components to transmit substantially only a wavelength band of said polychromatic radiation which is unaffected by changes in said sample component;
E. combining said two components with each other after said filtering, and
F. detecting the AC components of the combined signal for determining the amount of absorption by the one sample component.

22. A method for analyzing a fluid medium having at least one sample fluid, said one sample fluid having at least one characteristic absorption wavelength of interest, comprising the steps of:
A. passing a polychromatic electromagnetic radiation beam through said fluid medium;
B. dividing radiation exiting said medium into two time-varying components having a defined interdependent time-varying functional relationship;
C. filtering a first of said two components to transmit substantially only the one characteristic wavelength;
D. filtering a second of said two components to transmit substantially only a wavelength band of said polychromatic radiation which is unaffected by changes in said sample fluid;
E. combining said two components with each other after said filtering, and
F. measuring the AC components of the combined signal for determining the amount of absorption by the one sample fluid.

23. A gas detection apparatus for detecting, in a gaseous medium, at least one sample gas having a characteristic absorption wavelength of interest, comprising:
a gas sample chamber having an optical path passing therethrough,
means for positioning said chamber in the path of a beam of electromagnetic radiation, including radiation at least at said one characteristic wavelength and at a reference wavelength, for passing said beam through said chamber along said optical path,
means for modulating said beam exiting said chamber for forming at least first and second time-varying component beams, first filter means in the path of the first component beam for passing substantially only radiation of said characteristic wavelength,
second filter means in the path of the second component beam for passing radiation at at least said reference wavelength and not including said characteristic wavelength, and
means for combining said first and second wavelength component beams exiting said respective filter means for providing a detection signal characteristic of the quantity of said at least one sample gas.

24. A gas detection apparatus for detecting, in a gaseous medium, at least one sample gas having a characteristic absorption wavelength of interest, comprising:
beam modulation means in the path of a directed beam of electromagnetic radiation including radiation at at least said one characteristic wavelength, for providing a reflected and a transmitted component beam whose intensities vary 180° out of phase at the rate of repetitive movement of said beam modulation means, said means comprising
a planar member having a reflectance and a transmittance with respect to said beam which vary across its surface, and
means for repetitively moving said member within said path,
a sample gas holding chamber having a first optical path passing therethrough,
means for positioning said sample chamber in the path of one of said reflected and transmitted component beams for passing said one component through said sample chamber along the sample chamber optical path passing therethrough,
a reference gas holding chamber having a second optical path passing therethrough,
means for positioning said reference gas chamber in the path of the other of said reflected and transmitted components for passing said other component beam through said reference chamber along the reference chamber optical path passing therethrough, and
means for combining said reflected and transmitted components after passage through said sample gas holding chamber and said reference gas holding chamber for providing a detection signal characteristic of the quantity of said at least one sample gas.

25. A gas detection apparatus for detecting, in a gaseous medium, at least one sample gas, said medium having a plurality of characteristic absorption wavelengths of interest, comprising:
means for filtering an incident beam of electromagnetic radiation including radiation at at least two of said characteristic wavelengths to produce a sequence of single component beams at successive ones of said plurality of characteristic wavelengths, said filtering means having
a planar element having a plurality of narrow bandwidth filtering sections arranged in a predetermined manner, and
means for selectively moving said element relative to said radiation beam to sequentially position each respective filtering section in the path of said radiation beam;
beam modulation means in the path of said filtered beam for providing a reflected and a transmitted component beam whose intensities vary 180° out of phase, at the rate of repetitive movement of said beam modulation means, said modulation means comprising a member having a reflectance and a transmittance with respect to said filtered beam which vary across its surface, and means for repetitively moving said member within said path, a sample gas holding chamber having a first optical path passing therethrough, means for positioning said sample chamber in the path of one of said reflected and transmitted component beams for passing said one component through said sample chamber along the sample chamber optical path passing therethrough, a reference gas holding chamber having a second optical path passing therethrough, and means for positioning said reference gas chamber in the path of the other of said reflected and transmitted components for passing said other component through said reference chamber along the reference chamber optical path passing therethrough, means for combining said reflected and transmitted components after passage through said sample gas holding chamber and said reference gas holding chamber for providing a detection signal, time sequentially characteristic of the gas medium absorption for each filtering section.

26. A gas detection apparatus for detecting, in a gaseous medium, at least one sample gas, said medium having a plurality of characteristic absorption wavelengths of interest, comprising:

means for filtering a beam of electromagnetic radiation including radiation at at least two said characteristic wavelengths to produce a sequence of single component beams at successive ones of said plurality of characteristic wavelengths, said filtering means having a rotatable planar element having a varying narrow bandwidth filtering characteristic arranged in a predetermined manner; and means for selectively moving said element relative to said radiation beam to position said respective filtering characteristics in the path of said radiation beam;

beam-forming means supported in the path of said filtered beam for providing a first and a second component beam whose intensities vary 180° out of phase with each other, a sample gas holding chamber having a first optical path passing therethrough positioned in the path of one of said first and second components for passing one said component through said sample chamber along the sample chamber optical path passing therethrough, a reference gas holding chamber having a second optical path passing therethrough positioned in the path of the other of said first and second components for passing said other component through said reference chamber along the reference chamber optical path passing therethrough, means for combining said first and second components after passage through said sample gas holding chamber and said reference gas holding chamber for providing a time sequential detection signal characteristic of said gas medium at said successive filter frequencies.

* * * * *